United States Patent [19]

Ferreira

[11] 4,141,367
[45] Feb. 27, 1979

[54] CARDIAC ELECTRODE/PACER SYSTEM ANALYZER

[75] Inventor: Lloyd A. Ferreira, Williamsville, N.Y.

[73] Assignee: Med Telectronics Ltd., Suffield, Conn.

[21] Appl. No.: 792,404

[22] Filed: Apr. 29, 1977

[51] Int. Cl.$^2$ ............................................. A61N 1/32
[52] U.S. Cl. ............................................. 128/419 PT
[58] Field of Search ................. 128/419 PT, 419 PG, 128/2.06 R, 2.1 Z

[56] References Cited

U.S. PATENT DOCUMENTS

| | | | |
|---|---|---|---|
| 3,135,264 | 6/1964 | Tischler et al. | 128/419 PG |
| 3,523,539 | 8/1970 | Lavezzo et al. | 128/419 PG |
| 3,757,790 | 9/1973 | Herrmann | 128/419 PT |
| 3,768,014 | 10/1973 | Smith et al. | 128/419 PT |
| 3,768,487 | 10/1973 | Rose | 128/419 PT |
| 3,769,986 | 11/1973 | Herrmann | 128/419 PT |
| 3,782,367 | 1/1974 | Hochberg et al. | 128/419 PT |
| 3,885,552 | 5/1975 | Kennedy | 128/419 PT |
| 3,920,005 | 11/1975 | Gombrich et al. | 128/419 PT |

FOREIGN PATENT DOCUMENTS 2216043  10/1973  Fed. Rep. of Germany .... 128/419 PT

*Primary Examiner*—William E. Kamm
*Attorney, Agent, or Firm*—Gottlieb, Rackman & Reisman

[57] ABSTRACT

An instrument for detecting and measuring various characteristics of cardiac pacers and electrodes and visually displaying such measurements selectively on a digital display includes pacer analyzer means for measuring and displaying characteristics of a pacer, such as rate, pulse width, peak voltage and trailing edge voltage, electrode analyzing means for measuring and displaying characteristics of an installed electrode, such as impedance and intrinsic and evoked R-wave voltages and internal pacer means including means for adjusting pacer impulse rate and voltage and means for measuring and displaying various pacer characteristics of the internal pacer impulses, such as rate, voltage and amperage, a rechargeable battery for energizing the various circuits of the instrument and means for preventing externally supplied battery recharging electric power from communicating through the instrument with installed cardiac electrodes and with a pacer to be tested. Among the more important features of the instrument described are improved measurements of impedance and R-wave characteristics, which are considered to be broadly novel, illuminated (when activated) pushbuttons for actuating various measuring circuits, color coding of such buttons and arrangement thereof in separable banks or groups for ready identification and ease of operation, and an extra large digital display, visible across an average operating room so that a displayed measurement can be read by doctors or technicians at any of various locations in the room and the characteristics measured can be readily identified by observation of the pushbutton that is illuminated.

32 Claims, 22 Drawing Figures

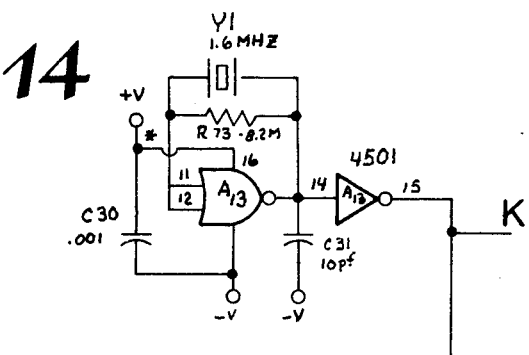
Fig. 14
Fig. 15
Notes:
(1) R41 & R42 are matched
(2) ✱ Wire as shown and/or very short
(3) # Shown on main frame p/L
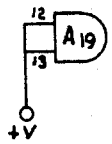
Fig. 16
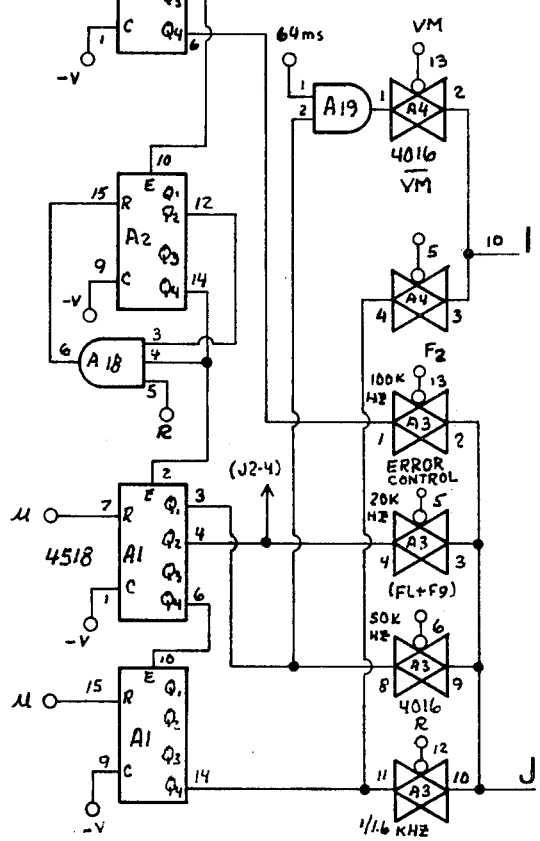
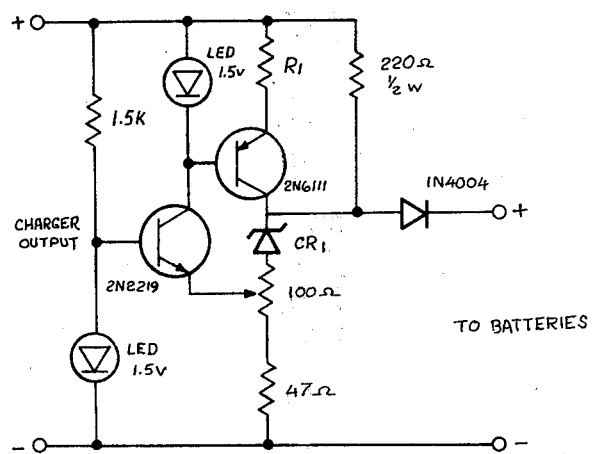

CARDIAC ELECTRODE/PACER SYSTEM ANALYZER

This invention relates to an instrument for measuring and displaying on a digital display various characteristics of cardiac pacers and electrodes. More particularly, it relates to such an instrument which is operated by a rechargeable battery wherein the recharging function is separated from the operating function so that it is impossible for recharging electrical power to be transmitted to an electrode under test (which may be implanted in a patient) and to an external cardiac pacer being evaluated. Very important features of the present invention include illuminated and color coded pushbutton actuation of various measuring circuits, large digital read-outs of such measurements and novel impedance and R-wave measuring and sensing functions (for ventricular inhibited pacers), plus other convenience and safety features.

It is known to be desirable to be able to test electrodes and electrode-heart site combinations when implanting electrodes and before installation of an implantable pacemaker. Of course, when testing the electrodes the leads to them are also being tested and therefore they will not be specifically referred to although it should be understood that when "electrode" is used in this specification, unless a different meaning is clear from the context, it is intended to relate to the leads-electrode combination. Various electronic diagnostic and analyzing instruments are well-known in the medical arts and sciences and cardiac pacers or pacemakers and electrodes have been tested using them, when installed, before installation and after removal. Electronic circuitry has been employed in various system analyzers and pushbutton switch operations and digital read-outs have been utilized. However, before the present invention there was not available so convenient a self-contained apparatus or instrument for automatically measuring characteristics of an external pacemaker and, with the help of an internal pacer, measuring characteristics of an electrode, usually when implanted, without the need for following more complex directions and/or making calculations, such as computing impedance from threshold voltage and current. Additionally, particular operations of the present instrument are novel in such instruments, such as impedance measurements at constant current. Furthermore, the operating dials and buttons of the present instrument are conveniently grouped and the various buttons are color coded and selectively illuminated so as to identify the function being measured and to facilitate simple and foolproof operation by technicians, rather than doctors and to warn by illumination of a particular color, e.g., red, when an electrode measurement is taken while support for a patient from an internal pacer is being suspended.

In accordance with the present invention there is provided a cardiac electrode/pacer system analyzer for use when implanting, testing and revising cardiac pacers and electrodes which displays any of a plurality of measurements of pacer and installed electrode functions selectively on a digital display which comprises: pacer analyzing means for measuring and displaying pacer characteristics, including a plurality of measuring circuits for measuring different characteristics of a pacer, a plurality of means for selectively completing the different measuring circuits when a pacer to be tested is connected to the pacer measuring circuit, means for connecting the pacer to be tested to the pacer measuring circuit and digital display means on which the selected pacer analyzer measurements are displayed when selected measuring circuits are completed; electrode analyzing means for measuring and displaying the impedance of an installed cardiac electrode, including a measuring circuit for measuring said impedance, means for completing the measuring circuit when an installed electrode to be tested is connected to the measuring circuit, digital display means for displaying the impedance reading when the measuring circuit is completed and means for connecting the installed cardiac electrode to the electrode measuring circuit; an internal pacer, useful for threshold analysis and for maintaining patient heartbeat, which comprises means for adjusting internal pacer impulse rate, means for adjusting internal pacer voltage, means for measuring at least one of rate, voltage and amperage of the pacer impulses, digital display means for displaying such measurement and means for connecting the implanted electrode to the internal pacer; a rechargeable battery for energizing the pacer analyzing measuring circuit, the electrode analyzing measuring circuit, the internal pacer and the digital display means; means for recharging the rechargeable battery from an external source of electricity; and means for preventing externally supplied battery recharging electric power from communicating with the means for connecting a pacer to be tested to the pacer measuring circuit and the means for connecting an installed cardiac electrode to the electrode measuring circuit. In specific preferred embodiments of the invention such analyzers are provided wherein novel structural features are present for measuring impedance and/or R-waves, for measuring pulse width and/or pulse peak and trailing edge amplitudes, for activating impedance and R-wave circuits (illuminated pushbuttons with depressed and elevated "active" positions) and for illuminating, locating and coding, so as to be readily visible, various activating pushbuttons. In broader embodiments of the invention such features are also included in electrode analyzers and/or pacer analyzers not necessarily of the more limited structure described above nor related to use with the heart. (The invention is also applicable to stimulating and pacing other body organs and tissues and analyzing their functions).

The invention will be readily understood from the accompanying description, taken in conjunction with the drawing in which.

Figure 17:
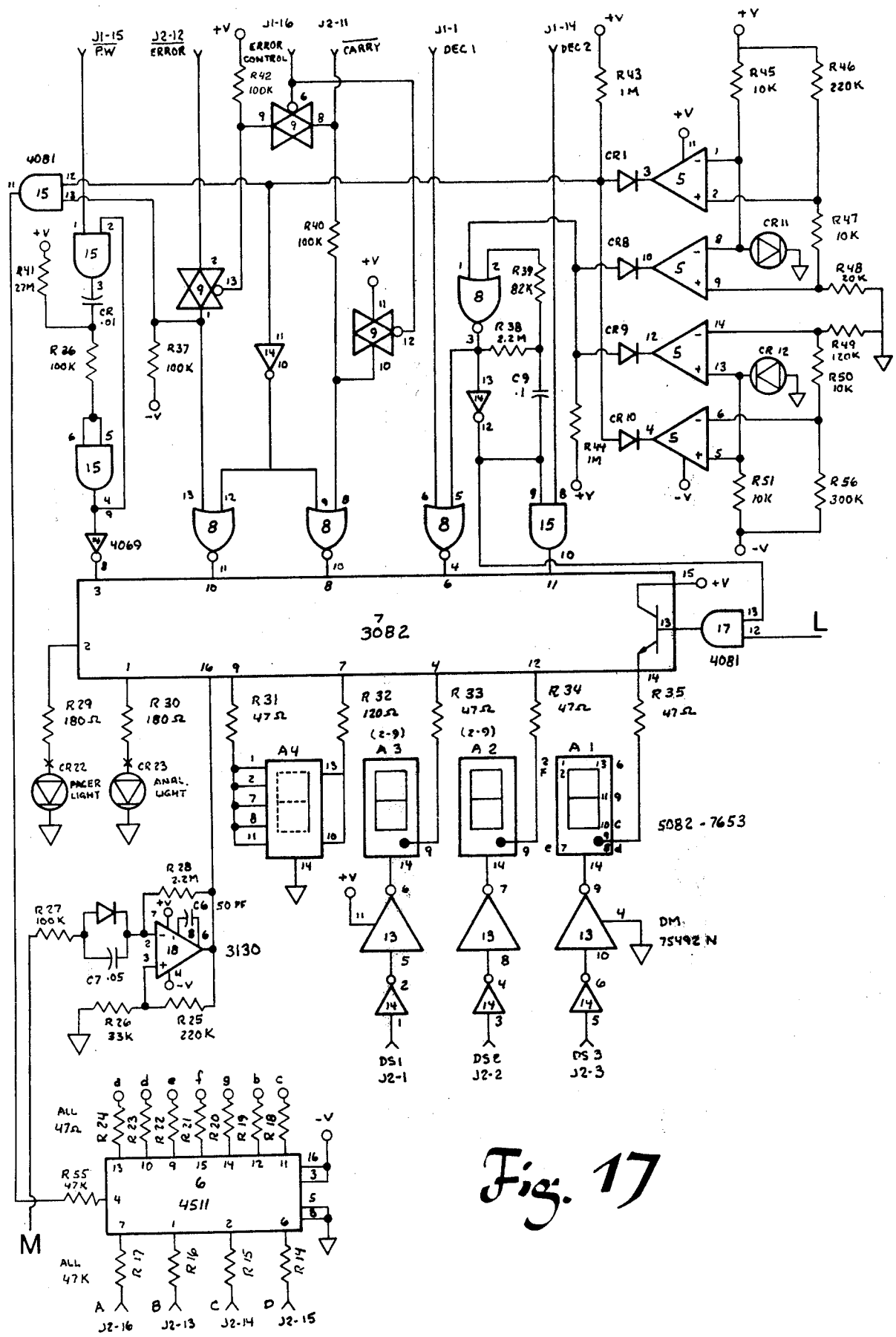
Figure 18:
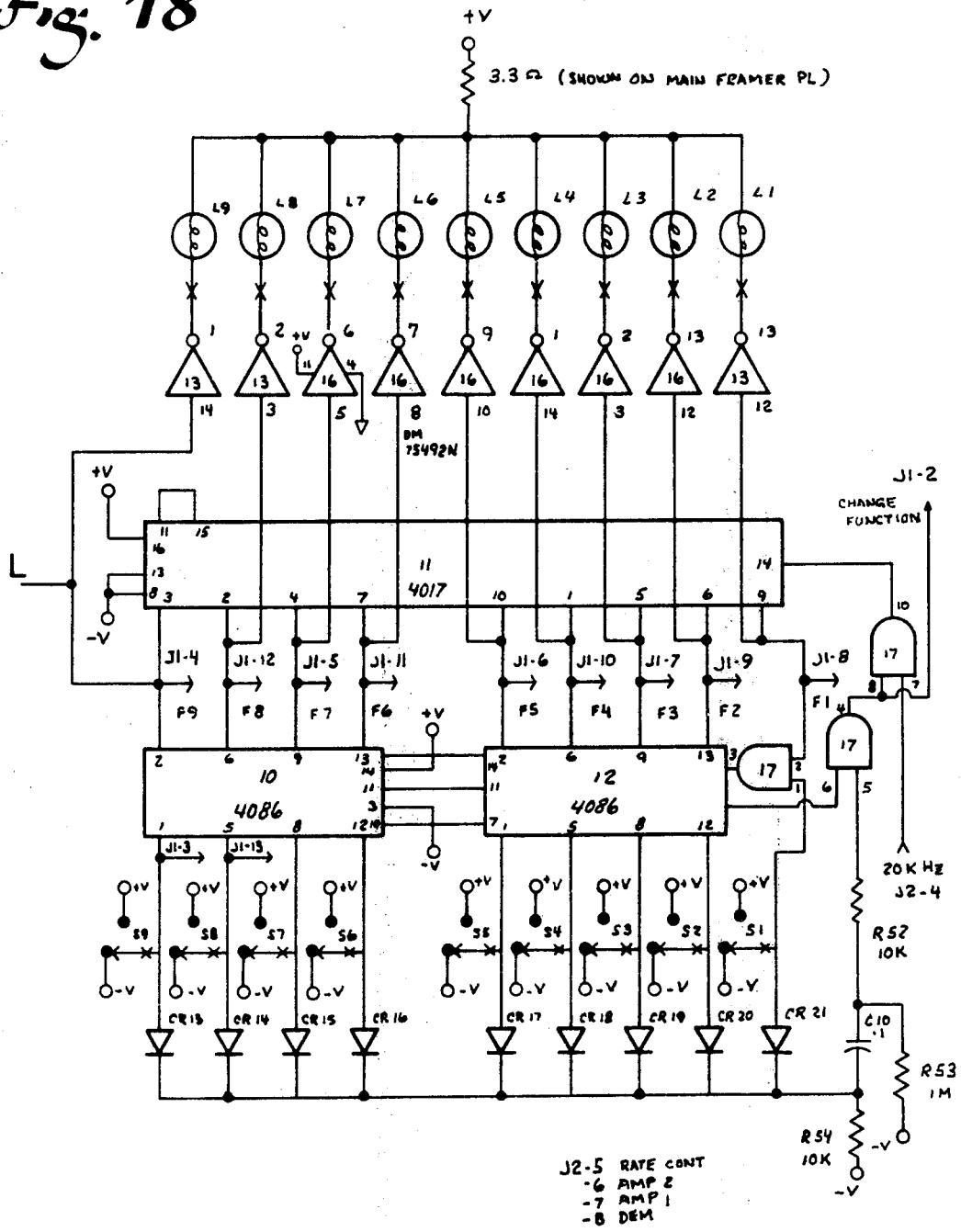
Figure 19:
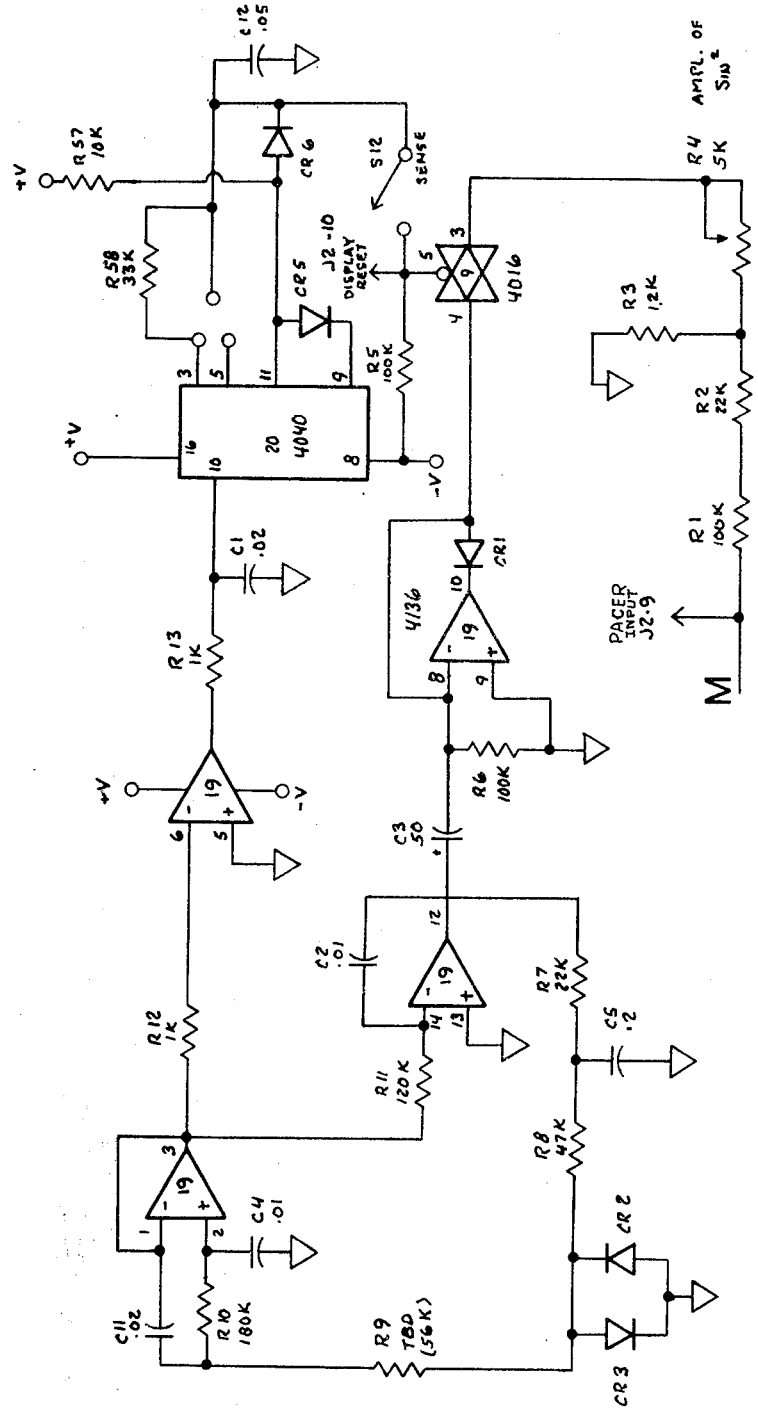
Figure 20:
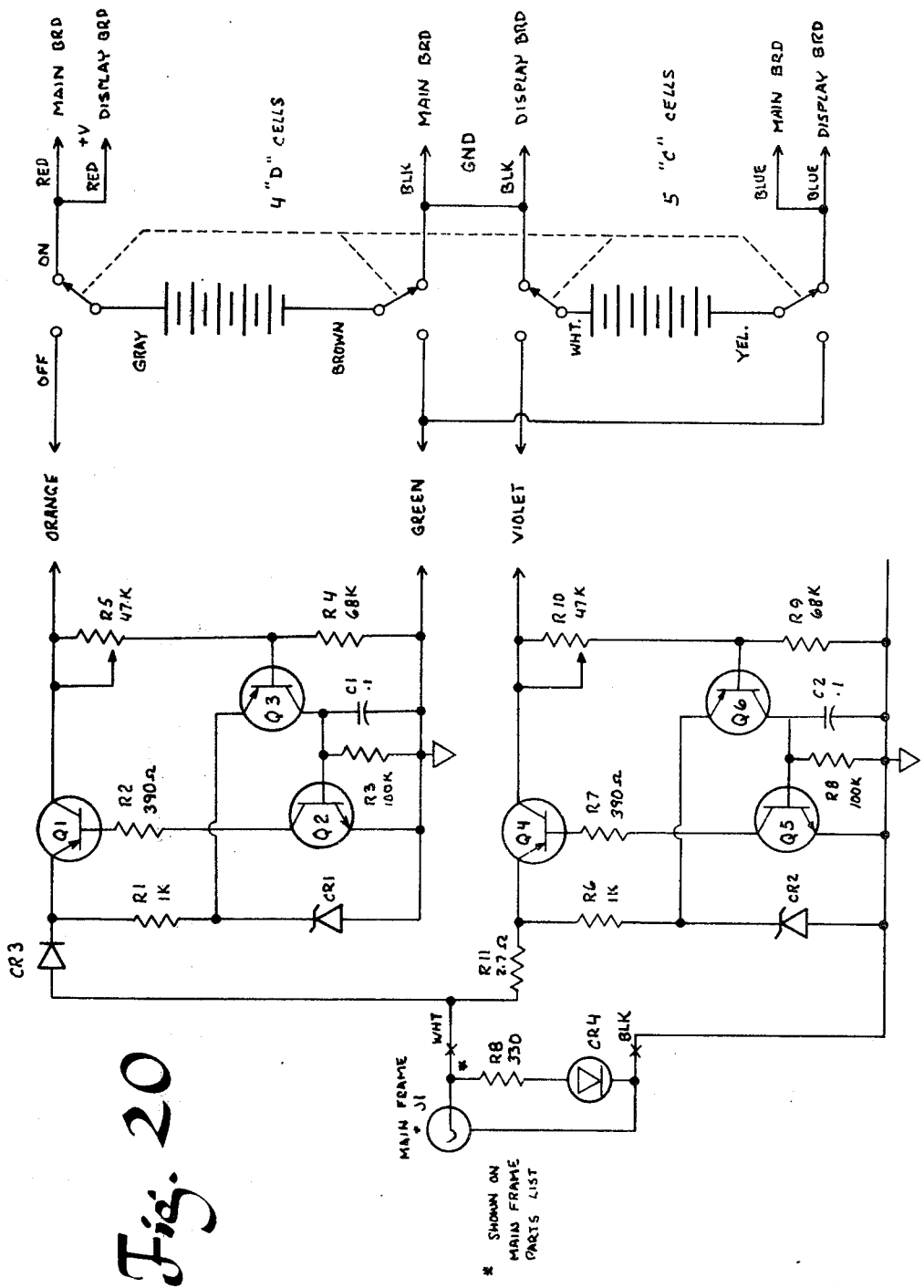
Figure 21:
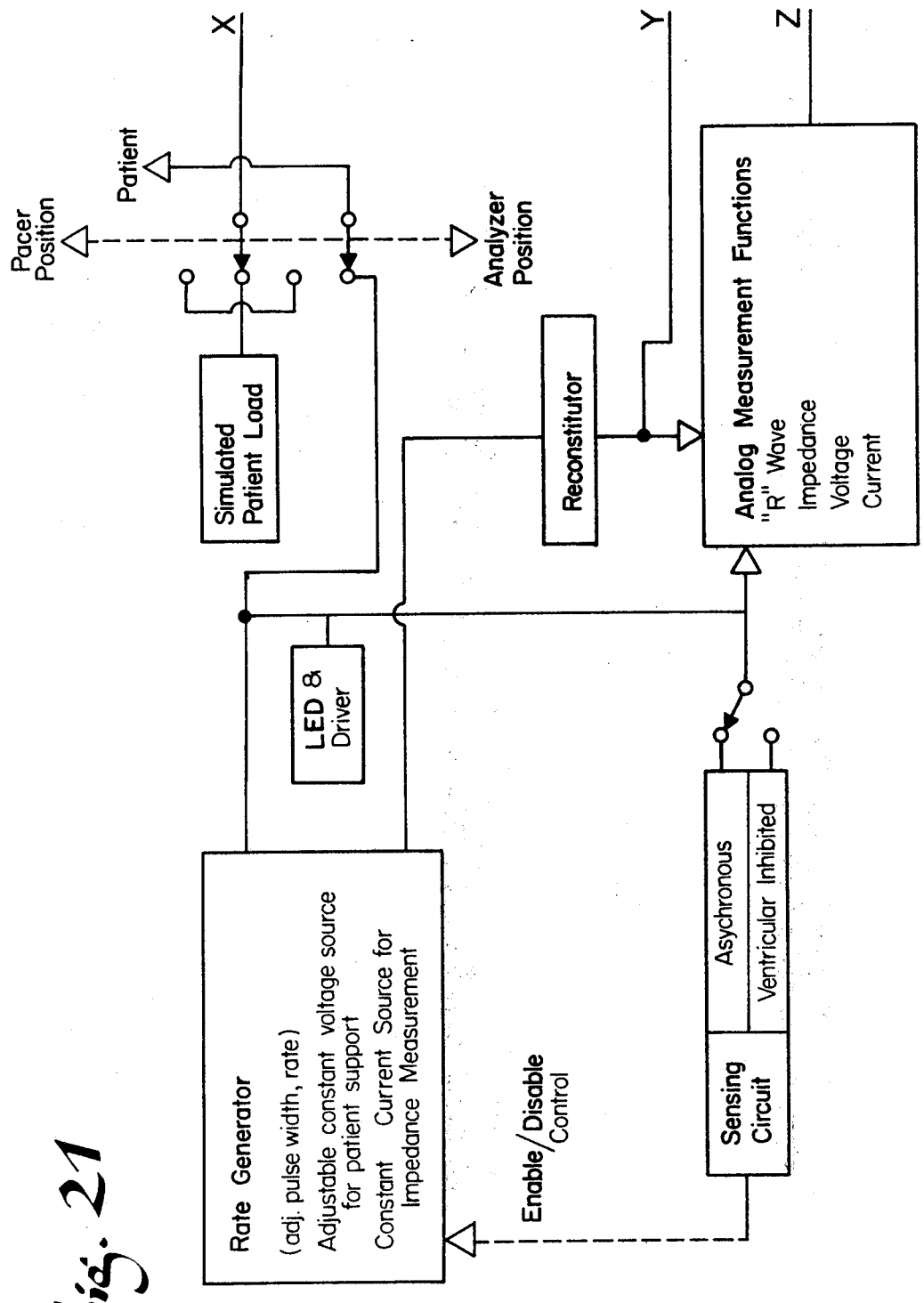
Figure 22:
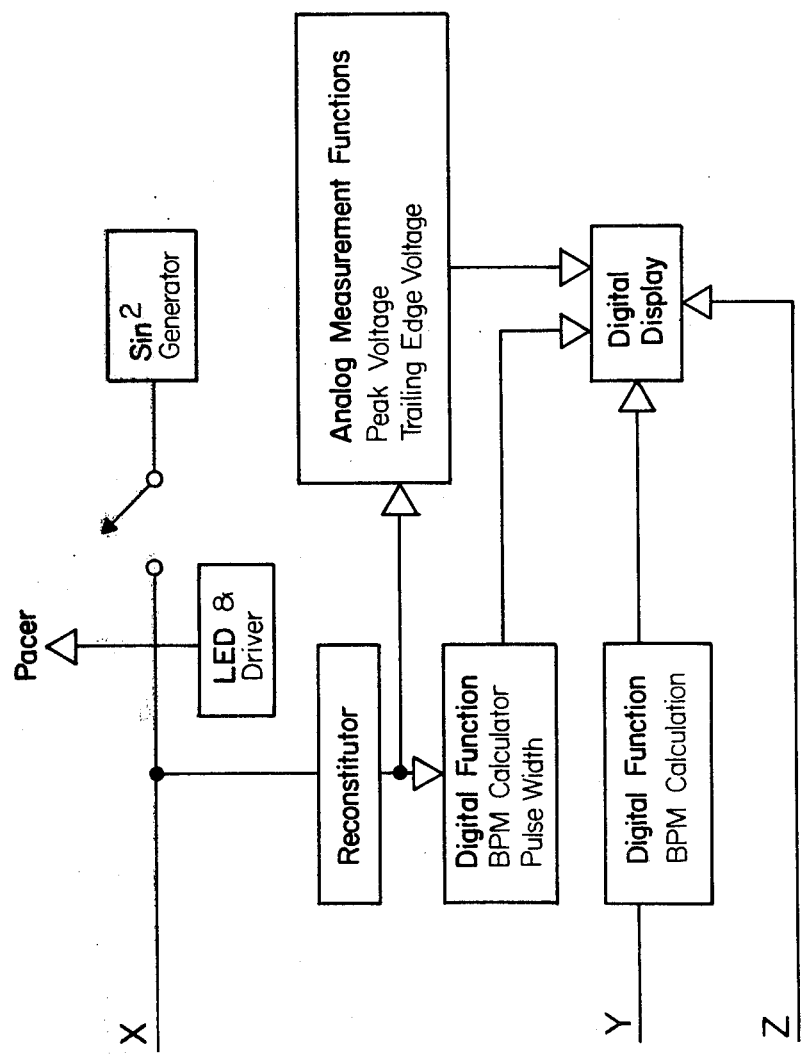

FIGS. 7–20 are various circuit diagrams of the apparatus or portions or components of such diagrams, with connecting lines between parts of single diagrams being indicated by similar letters (FIGS. 7–15 are for the main board, FIGS. 17–19 are for the display board and FIGS. 16 and 20 are for battery protection and regulator circuits); and FIGS. 21 and 22 are a functional flow chart in block diagram form, showing the interrelationships of circuit functions.

Figure 1:
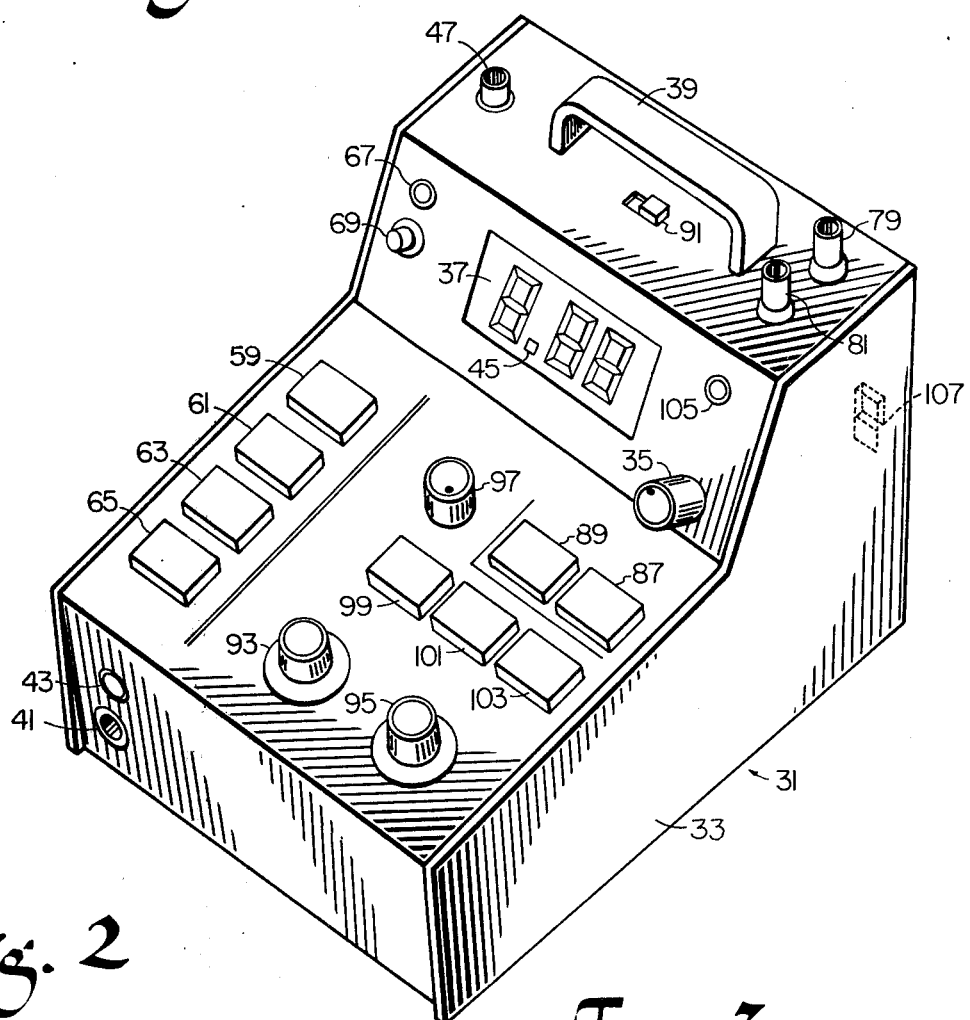
FIG. 1 is a perspective view of the apparatus of this invention, seen from above and front.
Figure 2:
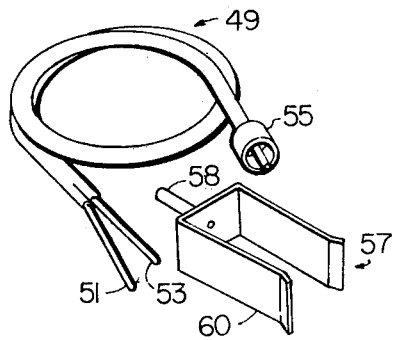
FIG. 2 is perspective view of a lead for attaching the apparatus to a bipolar pacer, with an adapter for converting an end of the lead to make it suitable for attachment to a unipolar pacer.
Figure 3:
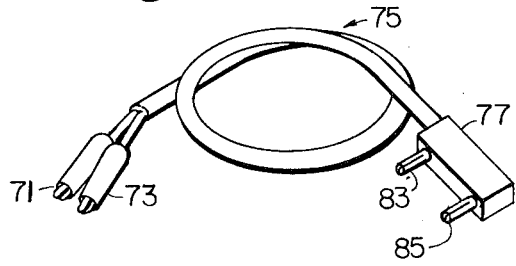
FIG. 3 is a perspective view of a lead for connecting the internal pacer and electrode analyzer sections of the apparatus to an implanted cardiac electrode.
Figure 4:
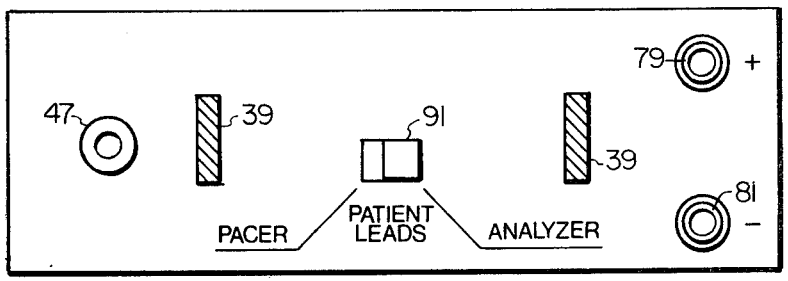
FIG. 4 is a top plan view of the upper level of the invented instrument, with the handle removed.
Figure 5:
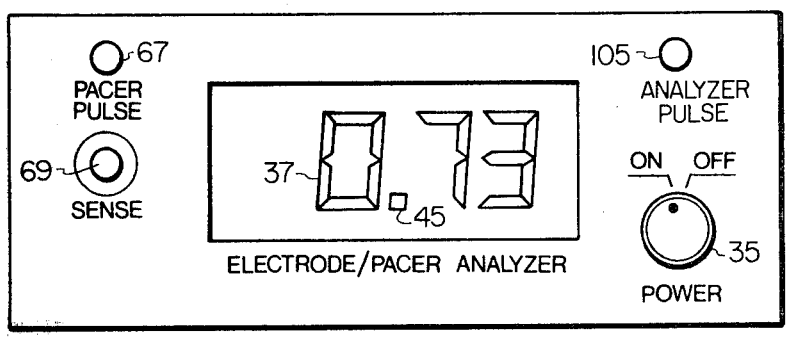
FIG. 5 is an essentially front elevational view of the digital read-out face portion of the apparatus, taken at a right angle thereto and with a digital read-out different from that of FIG. 1.
Figure 6:
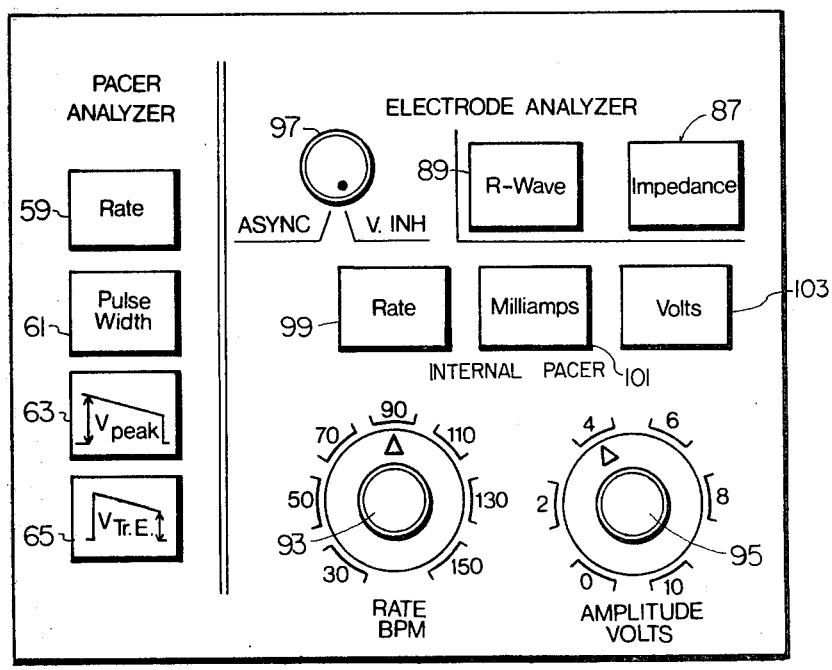
FIG. 6 is an essentially top plan view of the lower level of the pacer, taken at a right angle thereto.
Figure 7:
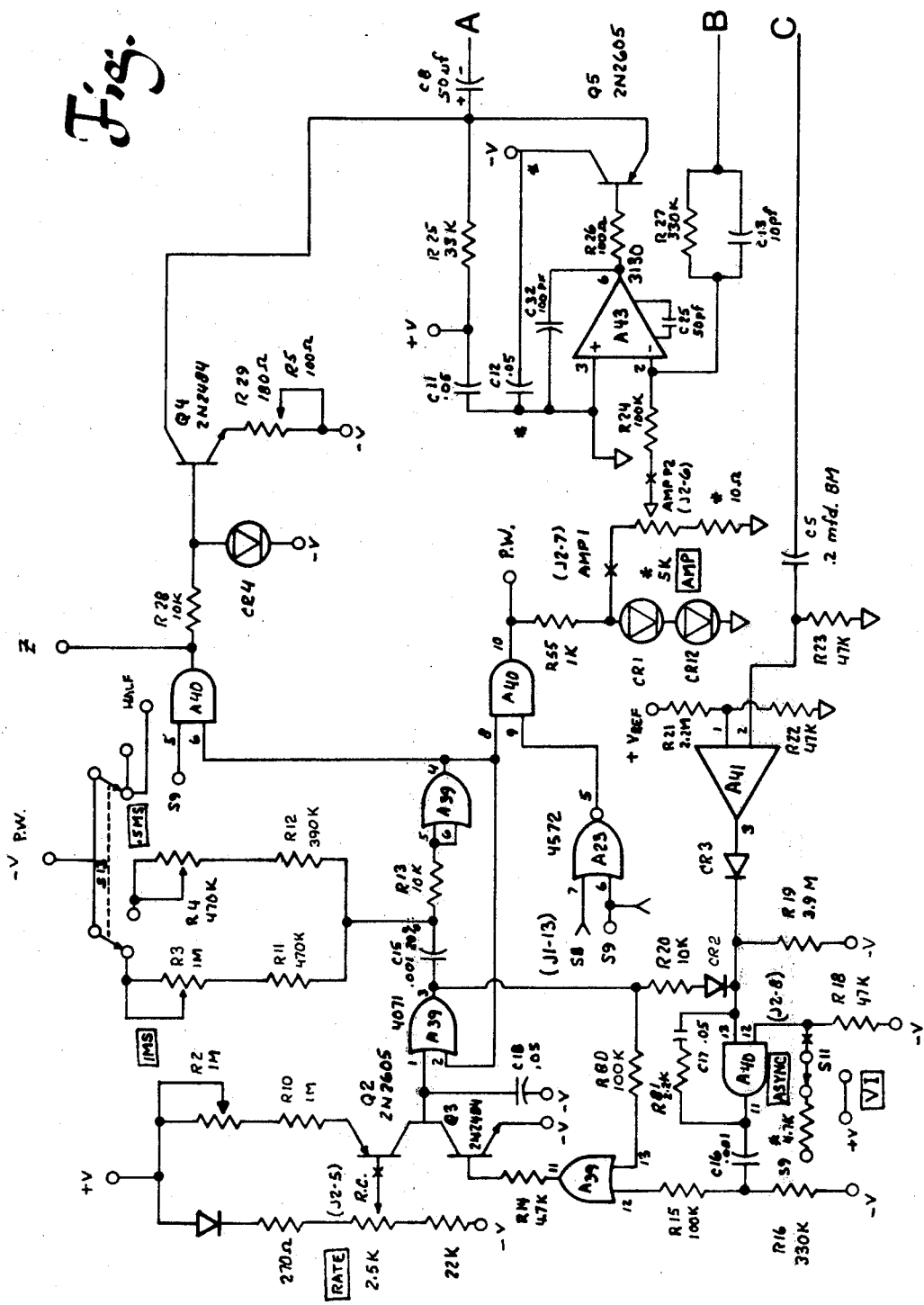
Figure 8:
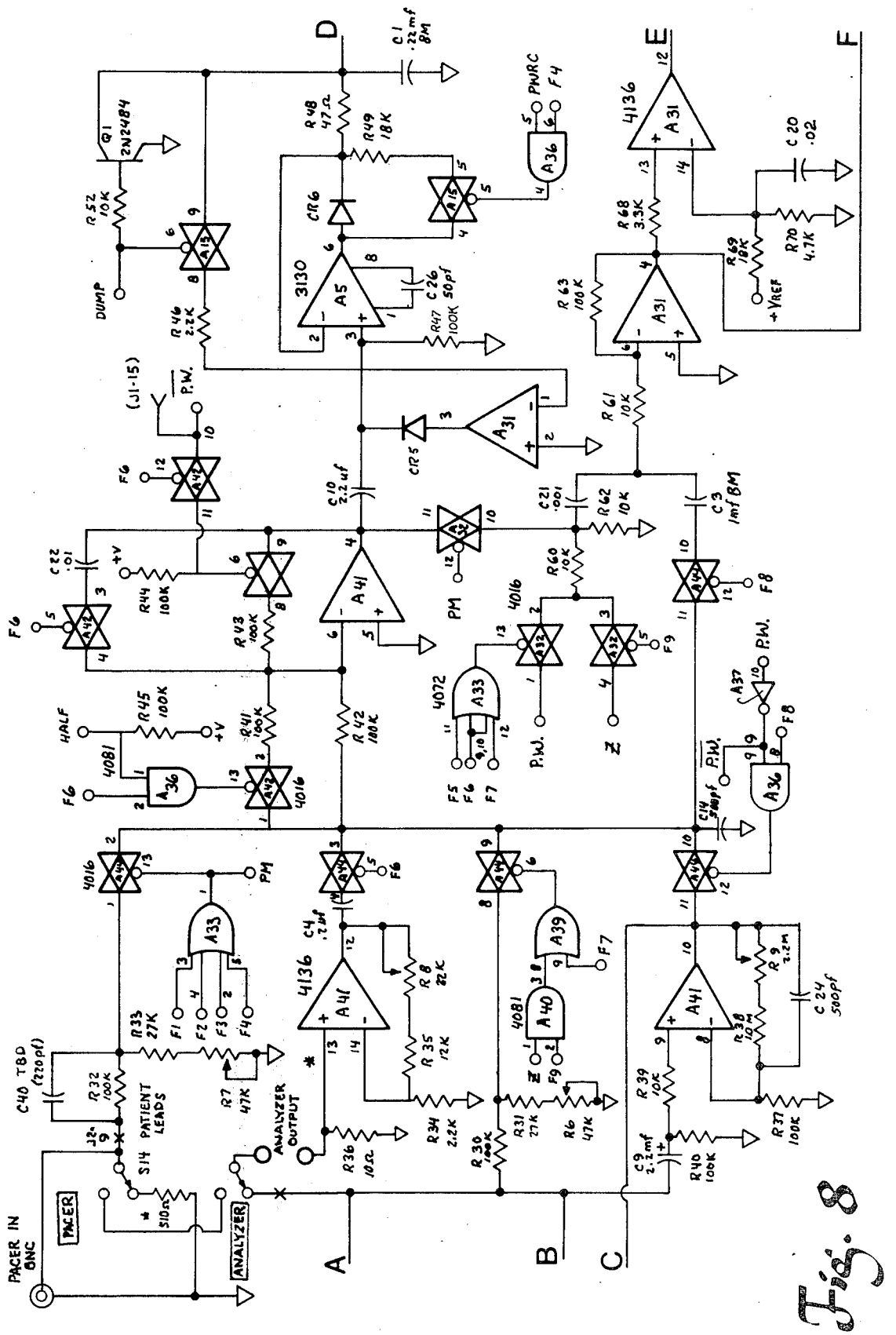
Figure 9:
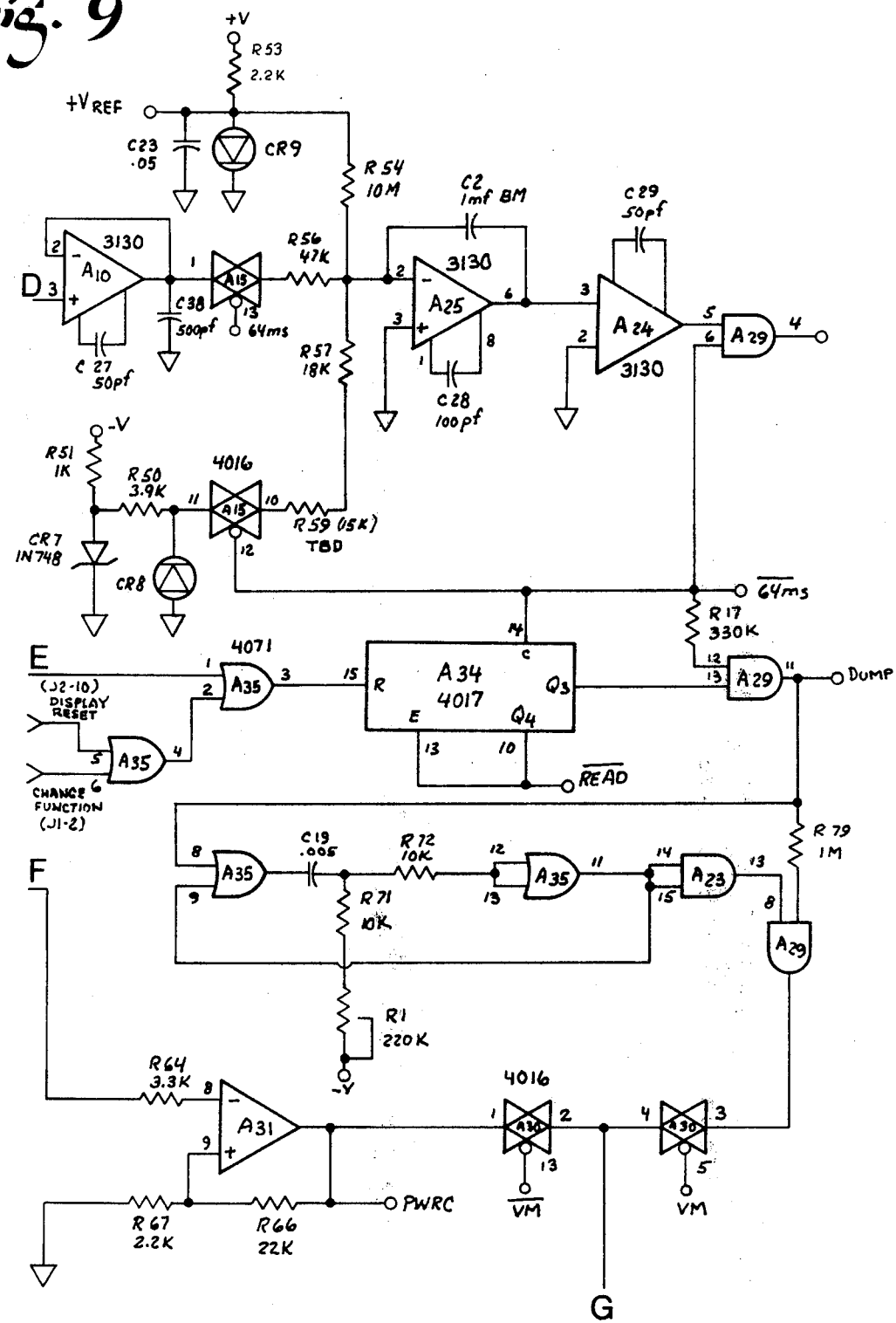
Figure 10:
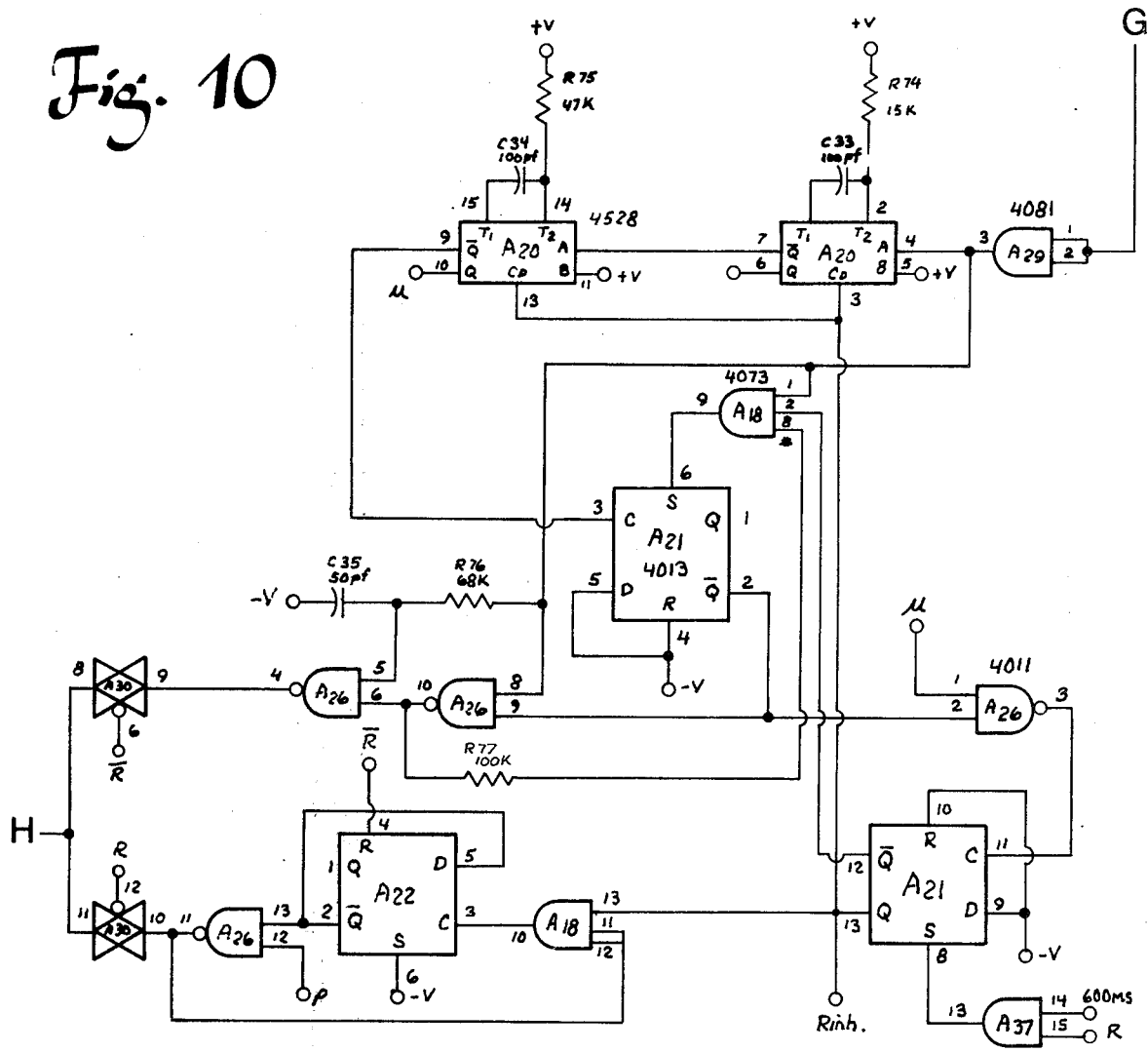
Figure 11:
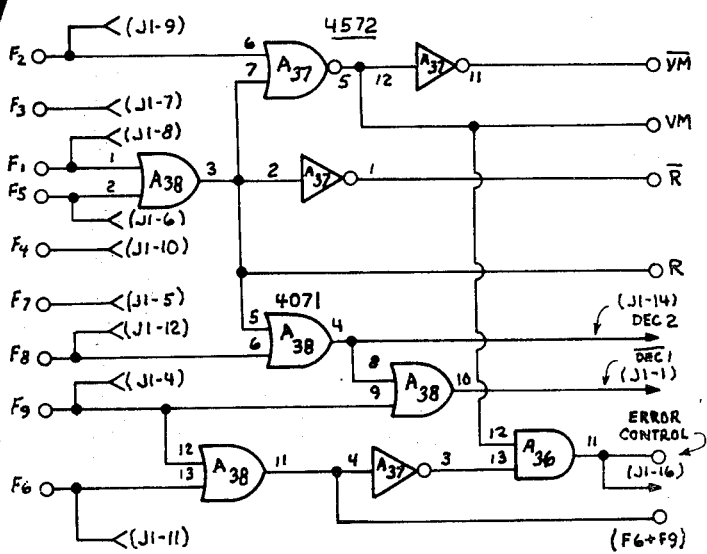
Figure 12:
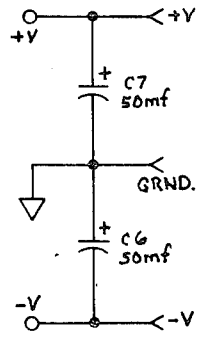
Figure 13:
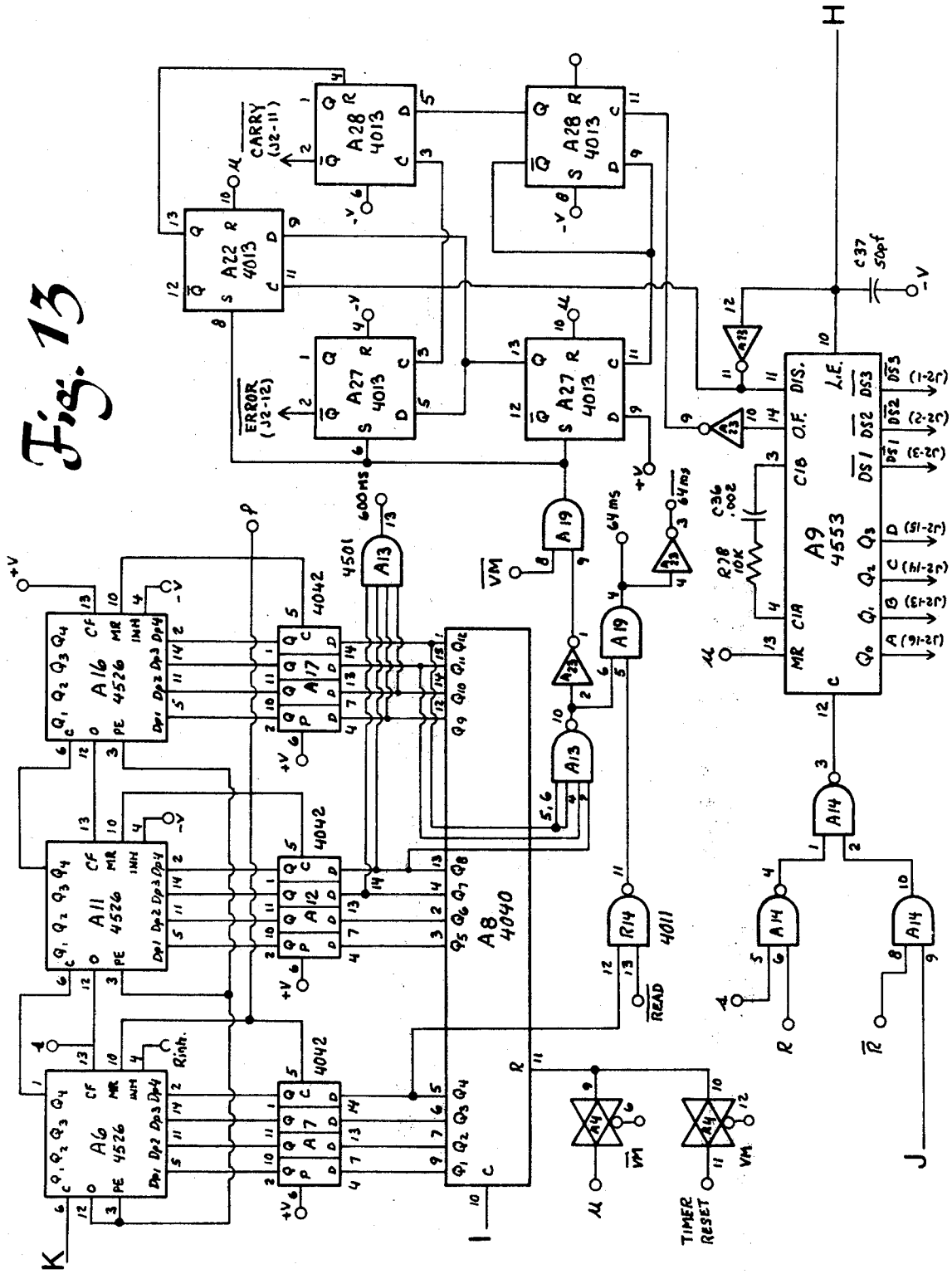

In FIG. 1 the cardiac electrode/pacer system analyzer 31 includes a casing 33, usually preferably of steel, alloy or other strong metal but it is contemplated that a synthetic organic polymeric plastic casing may also be employed, an on-off switch 35, a digital display 37, a carrying handle 39 and various other control knobs, selectors, buttons, lights, connections, switches, etc., which will be described in more detail subsequently. The parts shown in FIG. 1 are also clearly seen in FIGS. 4–6, together with indicia present, and such figures should be referred to in conjunction with the following recitation of parts and functions of the instrument shown in FIG. 1. By means of control knob 35 power to the component parts of the apparatus from an internal rechargeable battery, preferably a nickel-cadmium battery, is available when the switch is in ON position, to the left, as illustrated in FIG. 5. In such position internal circuitry prevents charging of the battery through battery charging socket or connection 41 and prevents external power brought to the apparatus via socket 41 from being transmitted to the internal mechanism of the apparatus or instrument and from it to a patient or to an external pacer. When switch 35 is in the OFF position power delivered to socket 41 is transmitted to the contained battery to be recharged (a charger of conventional type may be used) but has no access to other circuitry nor to the patient or an external pacer. When the battery is being charged signal light 43, preferably a light emitting diode (LED) is lit. Digital display 37 signals the desirability of charging the rechargeable battery by having the decimal point 45 thereof flicker to indicate low battery charge and subsequently if the battery is not recharged and is drained further, by having the entire digital display 37 turn dark (no-display condition) to indicate an even lower and possibly dangerously low battery charge. However, even when the display is dark the internal pacer will continue to function if the battery is strong enough so that a patient will not be disconnected from pacing by the machine.

Input terminal 47, preferably of press-and-turn or bayonet type, as illustrated, may be employed to connect an external pacer, not illustrated, to the instrument of this invention by means of lead 49, which has a pair of terminals 51 and 53 for connection to a bipolar pacer and a bayonet-type terminal 55 adapted to fit terminal 47. For connection of the apparatus to a unipolar pacer adapter 57 is employed, adapted to have conducting tube 58 thereof fitted in electrical contact over one of contacts 51 and 53 of lead 49 and to make electrical contact with the appropriate external portion of the unipolar pacer by means of spring clip 60. When the external pacer is connected to instrument 31 by means of input terminal 47 it is (normally) emitting a pulse which is analyzable by the pacer analyzing portion of the instrument, the operating buttons (or switches) whereof are on the left side of the instrument, the same side as the connection to the external pacer via input terminal 47 (intentionally so located for error-free operation). As is more readily seen in FIG. 6, depressable illuminated buttons 59, 61, 63 and 65, respectively for rate, pulse width, peak voltage and trailing edge voltage characteristics of the external pacer, are depressable to connect said internal circuitry to measure such characteristics selectively. When a button is depressed it becomes illuminated and remains illuminated when it returns to elevated position and when illuminated (and only one button is illuminated at a time) the particular measuring circuit is connected to the external pacer and the digital display reads out the measurement of the particular characteristic selected and corresponding to the illuminated button. Thus, the rate is read in beats per minute (BPM), the pulse width is read in milliseconds and the peak voltage and trailing edge voltage emitted by the external pacer are read in volts. The decimal point "floats" across the display, as warranted by the readings. When an external pacer is discharging to the analyzing instrument, light 67, a light emitting diode in normal circumstances, will be flashing, illuminated in synchronism with the pulses.

When the external pacer being tested is of the ventricular inhibited type as distinguished from the asynchronous type, for example, the function of the pacer may be checked to make sure that it is not emitting pulses when a heart R-wave of suitable magnitude to stimulate the heart on its own is present. Thus, the internal circuitry of the invented instrument is capable of transmitting to the external pacer via input terminal 47 a simulated R-wave impulse when sensing button 69 is depressed and held depressed. While button 69 is being activated a four millivolt amplitude simulated R-wave ($Sin^2$ type) is sent to the external pacer under test and if light 67 goes out while button 69 is depressed and is illuminated (it will flash at pulse frequency) when the button is released normal operation of the ventricular inhibited pacer is indicated, including reception of the simulated heart R-wave and suspension of pulse discharging from the pacer while the R-wave is being received.

The left side of the instrument, which, as shown, has the various test buttons grouped together in a bank, separate from other buttons and controls on the instrument so as not to be confusable with them, is most useful for testing an external pacemaker in the operating room shortly before that pacemaker is intended to be implanted in a patient. The ready portability of the invented instrument and its light weight, usually about 3 kilograms or less, make it convenient to employ and move about in the operating room while the illuminated test buttons thereof, the flashing signal lights and the large digital display, normally about two cm. high, make it possible for doctors in the operating room to be aware of the measurement being taken and the exact measurement although they are not adjacent to the instrument. In addition to being useful for measuring the characteristics of a pacemaker intended for implantation, as will be mentioned in more detail later the pacer analyzing section of the instrument may be employed for checking the output of the internal pacer of the instrument and the accuracy of some of the measuring functions of other parts of the instrument. Similarly, measurements made by the pacer analyzing or left hand section of the instrument may be checked by measuring functions associated with the internal pacer portion. Although both left and right hand sections of the instrument may utilize some common circuitry and are so arranged that only one measurement will be taken at a time, they may both be connected to their respective devices, the external pacer being connected to the input terminal and an implanted or about to be implanted electrode being connected to the output terminals, which will be described in more detail shortly, and selective readings with respect to properties of either the pacer or the electrode may be made. Thus, the instrument, while simple in operation, is sophisticated in structure and adaptable for a wide variety of useful functions.

In addition to measuring the characteristics of a pacer to make sure that it is acceptable for implantation it is also generally desirable to check various characteristics of the cardiac electrode after it is installed in intended working position in the heart but before connection thereto of the implanted pacer. Of course, the apparatus may be employed for testing uninstalled electrodes, as it may be for testing characteristics of pacers that have recently been removed from the patient for checking and repair, if necessary. However, in most instances electrode analysis will be of the installed or implanted electrode not connected to a pacer other than the internal pacer of the present apparatus. The lead(s) of the electrode (or electrodes), not illustrated, is/are held by alligator clips 71 and 73 of lead 75 and connector 77 thereof is adapted for press fitting into universal-type terminals 79 and 81 at the top of the apparatus by means of banana-type connectors 83 and 85. However, terminals 79 and 81 are also adapted to have the tops thereof screwed down on wires or leads which may be wrapped around central terminal posts or passed through central openings in the posts, so that the terminals are useful with a wide variety of lead designs (as may be terminal 47 or modifications thereof).

The electrode analyzing portion of the instrument, as illustrated, includes R-wave and impedance measuring capabilities. Impedance measurement pushbutton 87 is like those previously described, being of transparent material which is illuminated from below when the button is activated. In addition to impedance button 87, R-wave button 89 is also part of the electrode analyzing section and is, like button 87, color coded, usually red, to indicate that there is more care required in making such measurement, because, as will be described more fully later, patient support by the machine is temporarily suspended when impedance and intrinsic R-wave amplitude are being measured.

When impedance is being measured pushbutton 87 is depressed and held down for about 3 to 5 seconds. Upon release of the button it remains illuminated and the last impedance measurement, in ohms, is held on display 37 until another measurement is made. All measurements are held on the display in this manner until the machine is turned off or another measurement is taken. The method of measuring impedance requires no E/I calculation by the operator and additionally, has the advantage that the conditions of the pulse generator or internal pacer are set so that the variations in impedance over a period of time are indicative of changes in the installed electrode rather than of changed conditions such as different current flows, pulse widths, etc. When the impedance button is depressed the pulse transmitted to the installed electrode is in ventricular inhibited mode, irrespective of the mode switch 91 position and there is delivered to the electrode an accurately calibrated constant current pulse of 4 milliamperes (MA) and 0.5 millisecond (MS) duration. Thus, an absolute impedance value is obtainable, which is repeatable and therefore more meaningful over a long term. Especially because of the possibilities of encountering a variety of electrode types, of dislodgement of an electrode and breaking an electrode, for any of a number of possible reasons, a calibrated standard current pulse makes the impedance measured thereby more valuable for diagnostic, statistical and measurement purposes. The ventricular inhibited mode of the pulse delivered for impedance measurement is employed to prevent competition and a 4 MA pulse is used as a typical mid-range value to prevent nonlinearity which can be introduced due to polarization of electrodes by large current flows (4 MA is the typical current for a pacer using an eight square millimeter electrode, such as one of the ball tip design). Because in a small percentage of cases it is possible that the 4 MA, 0.5 MS pulse delivered when taking the impedance measurement might be inadequate for capture the button should never be held down for more than a few seconds and its color coding red reminds the user of the apparatus of this fact.

The R-wave button 89 also is illuminated when the apparatus is on and the button is the last (most recent) one that has been depressed. It is illuminated both in depressed and return positions. When depressed the pulse generator is disconnected and the patient is unsupported so that the intrinsic R-wave, in millivolts (MV) can be read. When released the reading will be of evoked or stimulated R-wave. Thus, it is important that the measurement of the intrinsic R-wave, which is that which a sensing type of pacer, such as a ventricular inhibited or ventricular synchronous pacer would sense, be recorded immediately and before releasing the push button. One spontaneous beat is all that is required to enable measurement of R-wave amplitude while the red button is depressed. An important feature of the R-wave measuring circuit, in combination with the digital display, is that if the intrinsic R-wave is below four MV it will not be indicated on the display and either an E (for error) signal will appear or a nonsense reading, sometimes corresponding to the last previous reading taken on the instrument, will remain on the digital display. (Note that E readings appear on the digital display when incorrect connections have been made or other operator error has occurred and when the measurement is outside certain prescribed ranges). The evoked R-wave reading is the amplitude in millivolts resulting from the artificial stimulation of a myocardium by the pulse generator. The orientation of the electrode and the condition of the surrounding myocardial tissue may cause the measured response to vary so as to be above or below the average expected from a spontaneous natural heart beat. Reading the evoked R-wave amplitude with the present instrument permits a rough estimation of such amplitude which might be seen in the future by an electrode implanted in a patient with no spontaneous heart beats at the time of implant.

In addition to the electrode analyzing section, on the right side of the instrument there is also contained a pulse generator or internal pacer section. This includes control dial 93 for regulating the pulse frequency (beats per minute or BPM) within the range of about 30 to 160 BPM and dial 95 for control of the voltage of the internal pacer within the 0 to 9.99 range. Thus, for example, in addition to setting the characteristics of the pulse generated the mentioned control knobs, measuring buttons and display can be utilized to determine the threshold potentials and current flows of the installed electrode (including the leads thereto). These and other measurements are measured with precision because of the accuracy of the digital read-out over the ranges thereof. To measure threshold the rate is set above the patient's pulse rate and the voltage is increased until capture is obtained, after which it is decreased until capture is lost (as may be measured by an EKG machine or by other means). The point at which capture is lost is the threshold voltage, preferably taken at an approximately normal pulse rate but in operation the voltage (and current) applied should usually be sufficiently higher than threshold to assure that there will be no inadvertent loss of capture.

Knob 97 may be moved to either asynchronous or ventricular inhibited position to alter the mode of the internal pacer.

Pushbuttons 99, 101 and 103 are respectively for the measurement of rate (BPM), milliamperes (MA) and volts and measure such characteristics of the pulse generated by the internal pacer. These buttons, like those of the left side of the instrument, are depressed to complete and activate particular measuring circuits and the most recent button pressed becomes illuminated and activated. Such buttons need not be held depressed and cause the digital display of the measurement whether they are held down or are allowed to return to original position providing they are the last activated (and illuminated).

Flashing light (LED) 105 indicates the frequency of the pulse generated by the internal pacer and, when either of buttons 87 or 89 is depressed, stops flashing to indicate that the patient might not be supported by the pulse generator.

At the top of the apparatus is switch 91 for connecting the external pacer or the analyzer (internal pacer) to the electrode. By moving switch 91 to the left, in the direction of the external pacer terminal, the external pacer is connected to the electrode, bypassing the internal pacer. When the switch is moved to the right, in the direction of the internal pacer portion of the instrument, the internal pacer is connected to the electrode or patient. Thus, it is a simple matter to switch such connections, as may be desired, which is especially important so that the physician can note the operation of the external pacer when actually connected to the implanted electrodes immediately before implantation of the pacer. If the pacer does not function properly when connected to the electrode it can be replaced without the necessity of a new implantation being effected.

Because most commercial pacers utilize a pulse width of about 0.5 or 1 MS switch 107 is provided at the rear of the machine as illustrated (but other locations may also be used) to allow for selection of the desired pulse width being generated by the present machine. Of course, instead of the two specific pulse widths mentioned, switch 107 and the associated circuitry may be modified so as to enable the selection of various pulse widths over broader or narrower ranges, with such selection being from either discrete or continuous values.

Case 33, as illustrated, is of metal but is completely insulated from all of the buttons, knobs, dials, lights, switches, terminals, leads and handle so as to prevent any shorting out of a portion of the circuit due to a charge being applied to the casing and also to prevent any such charge being applied to the casing from the battery charger, the battery or other internal circuitry. Most important, the casing is insulated from the battery charger and is not employed as a common ground as is often done in various electronic apparatuses. Rubber feet, not shown, support the instrument and insulate it from any base on which it may be rested. The entire unit, including the portions shown, back, side and bottom, is sterilizable with ethylene oxide without any damage to the internal circuitry and to help maintain sterility, the unit is comparatively easy to keep in clean condition.

Operation of the present apparatus is extremely simple and may be undertaken by technical personnel, paramedics and nurses, in addition to doctors. Error is prevented by the foolproof nature of the instrument and by the absence of any necessity for making calculations. Following is a summary of the various functions of the different parts of this system, after which a more detailed example of an instruction and record procedure that can be utilized will be given, followed further by variations of the present structure and additional descriptions of it and such variations.

Rate measurement in BPM and pulse width measurement in milliseconds of a pulse generator or external pacer may be readily taken and the output pulse amplitude (leading and trailing edges) in volts may be measured simply by depression of the appropriate buttons and reading of the digital display. The pulse generator sensing circuit may be checked with a simulated R-wave and by observation of the LED which indicates pulse delivery when flashing or pacer inhibition when flashing is momentarily halted during checking of the sensor circuit. The pulse generator may be held in a sterile field and may be electronically switched through to communication with the implanted electrode for verification of pacing and sensing prior to implantation of the pacer.

The electrode system may be analyzed for cardiac R-wave amplitude (in millivolts), both intrinsic and evoked, by pushbutton operation, and for impedance of the electrode system (constant current), which is displayed in ohms. The electrode may be checked for proper functions in cooperation with the pulse generator about to be implanted by switching the control prior to insertion of the pacer, as mentioned above.

Threshold analysis may be carried out either in asynchronous or ventricular inhibited pacing mode as best suits the etiology of the patient. Voltage thresholds may be measured and displayed to 1/100 volt and current thresholds may be measured and displayed accurate to 1/10 MA. There is a choice of 1 MS or 0.5 MS pulse widths to match the characteristics of the pacemaker to be implanted or to match previous measurement criteria. The pulse generator rate may be varied between 30 and 160 BPM as desired, with an accuracy of 1/10 BPM.

The adjustable internal pacemaker may be operated in ventricular inhibited or fixed rate mode and may be used with either unipolar or bipolar electrodes. As is the situation with respect to threshold measurements, the rate is adjustable between 30 BPM and 160 BPM, the voltage output is adjustable within the 0 to 10 volt range, the pulse width can be regulated to be 1 MS or 0.5 MS and flashing of a light emitting diode indicates delivery of a pacing pulse.

Among the generally desirable features of the instrument is safe eight-hour rechargeable battery operation with independent charge indicator and recharge need indicator. Self-testing is provided by utilizing separate circuitry for pulse generation and pulse generator analysis. In self-testing the output and imput terminals are connected and internal pacer characteristics can be read with the aid of the "external circuitry" and vice versa. The case is isolated from the circuits for defibrillation protection. The unit is adaptable for use with various autoclavable connecting cables to fit a wide variety of pacers and electrodes, probably almost all that are available. Rapid trouble shooting is facilitated by the simplicity and accuracy of the instrument. Illuminated pushbutton switches allow immediate indication of the test mode in use from a distance, such as across an operating room. The entire apparatus may be ethylene oxide gas sterilized and it is of convenient size, weight and shape for use by any of the staff in the operating room or catheterization laboratory.

Although normal operating procedure utilizing the present instrument will be specific to particular implanting teams and will be adapted to their needs and techniques the following procedure is one in which the system analyzer is preferably employed.

The analyzer should be left on charge and not in use for about an eight to twelve hour period once a week. The red light adjacent to the recharger socket indicates when charging is in progress. After completion of charge the charger plug should be removed before using. At this time, with the plug removed, the unit should be checked to make sure that it is functioning satisfactorily. This may be done by turning the ON-OFF switch to ON position and noting the appearance of the digital display. If it is illuminated and the decimal is not flashing the unit is ready for use. Next, autoclaved connecting leads are placed in a sterile field with the pulse generator (external), electrode lead and any necessary adapters and the electrode is implanted. The slide switch is to the right, in analyzer mode and the patient is paced through connecting leads with the adjustable internal pacemaker at a selected appropriate rate, voltage output, pulse width, etc. The voltage and current, set at rates suitable for establishing capture, are measured and recorded, after which the impedance and R-wave amplitudes are measured and recorded. Then the internal pacemaker outputs are re-set to appropriate levels to ensure safe artificial pacing support for the patient through the installed electrode while other tasks, hereinafter described, are performed.

A new implantable pulse generator to be installed or an explanted old pulse generator being evaluated is connected to the instrument on the left side thereof, with the slide switch still in the analyzer mode position, and rate, pulse width, peak voltage and trailing edge voltage are measured, recorded and compared to specifications to make sure that the pacer to be installed is satisfactory. Before disconnecting the new pacer from the instrument, slide the patient lead selector switch to the left to the pacer position so as to connect the new pacer to the implanted electrode and in such position check the proper function of the whole system for sensing (for ventricular inhibited pacers) and pacing. Upon satisfactory sensing and pacing being observed remove the new pacer from connection to the test leads, connect it to the installed electrode and implant the complete system. After completion of the operating procedure the analyzer should be wiped clean with a damp cloth, the connecting leads should be resterilized and the recharger should be plugged in with the analyzer kept on charge. The analyzer should be checked periodically by connecting the terminals that would go to an implanted electrode to the bayonet type connector and moving the slide switch to the analyzer position, making certain that the black terminal (the forward negative terminal), is connected to the center pin of the bayonet type connector.

Although the apparatus and its operation have been described, more detail about certain functions will now be given. Safety features have been built into the instrument to prevent charging electric power from affecting the circuitry or a patient connected to the analyzer but still the analyzer should not be used with the recharger connected to it. The digital display is a 3½ digit display and provides accurate presentation of the data obtained as each parameter is measured. Various ranges of measurements that may be displayed without going beyond the range of the instrument are from 30 to 200 BPM, 0 to 10 volts (volts, peak voltage and trailing edge voltage), 0 to 100 MA, 0 to 100 MV (R-wave), 100 to 2,000 ohms and 0.01 to 10 MS (pulse width).

The multipurpose universal terminals employed to connect the implanted patient electrode to the outgoing stimulating pulses generated by the adjustable internal pacemaker and the incoming pulses sensed from the patient by the electrode to the analyzer are red for the indifferent, plus electrode and black for the stimulating, negative electrode. The terminals are spaced apart so that the most common commercially employed leads fit them directly but they also have means for fitting bared electric wire, plug-in jacks, etc. In connection with the handling of any uninsulated electrical wires which connect directly and invasively to the heart or surrounding tissue care should be taken to avoid contact with poorly grounded or uninsulated electrical equipment used in the vicinity of the patient to avoid any shocking which might be capable of causing ventricular fibrillation.

The sensing device to determine the responsiveness of an external ventricular inhibited pacer to an R-wave initiates a train of simulated R-waves at a rate of approximately 140 BPM when the contact button is pushed. If the pacer is operating properly it will usually be inhibited (or synchronized) with the train of simulated R-waves, thus causing the light to stop flashing in the usual case, but it also may flash at the high rate (140 BPM), indicating proper sensing amplifier operation. For those pacers wherein a ventricular inhibited unit has a tracking pulse, e.g., Telectronics 120 or 140 and Starr Edwards, the pacer pulse light will flash at 140 BPM as it is triggered by the tracking pulse. This also indicates that the amplifier will sense R-waves which exceed approximately 4 MV. The rate measurements which may be obtained in the laboratory, with pacers operating at room temperature, rather than 37° C., will usually be below their actual operating rates when implanted in the body, for example, by two or more BPM, and this should be taken into account. The pulse width generated and measured by the machine is not normally temperature dependent. The peak voltage is automatically measured at the peak of the pulse being delivered, which is usually at the leading edge or near the leading edge and nearly always is over 5 volts. The trailing edge voltage is typically about 5% lower than the peak voltage. Together, the two measurements allow the doctor to visualize the shape of the delivered pulse without the use of an expensive oscilloscope. Both tests are done under a typical physiological load of about 500 ohms and hence the results are a verification of a pacer's ability to perform under load. Alternatively, if the slide switch is moved to the pacer mode the patient's own load may be introduced.

When maintenance of sterility of the pacer and analyzer is important it is preferable to enclose the whole unit in a sterile transparent pliable plastic bag and to operate all the controls from the outside of the bag. The present instrument is remarkably safe for use, even in explosive operating room atmospheres, because the voltages used do not normally exceed 6 volts DC but because of remote possibilities of malfunction, overheating or sparking, all reasonable and legally required precautions should be exercised in the presence of combustible materials.

The electronics and circuitry of the invention have been described in detail in FIGS. 7–22 with respect to a highly preferred embodiment thereof so as to make the operation of the invention clear to one of skill in the art viewing those figures. Because of the numerous component parts, separate recitations and discussions of each of them and of their functions have been omitted and reference should be made to the drawing, which is sufficiently complete to explain the invention. However, with respect to selected features considered to be of special uniqueness and importance some additional discussion of the electronics and of the advantages of the novel features is considered to be useful. In the circuitry for measuring pulse width a unique electronic technique is employed which utilizes a reconstitutor which is sensitive to fast rises and falls of voltages. Thus, the duration of the pulse is measured from the beginning of a fast rise in voltage to the beginning of the following fast fall, not between any pre-selected voltages on the rise and fall curves. Such technique is considered to be more accurate and gives a result which is more representative of the true effective pulse width. The method of peak and trailing edge amplitude measurements is considered to be unique because the actual peak and trailing edge voltages are measured rather than the amplitudes at particular preselected wave locations thought to correspond to the peak and trailing edge, such as 50 to 90 microseconds into the wave form. The employment of a $sin^2$ wave generator produces a wave which is more peaked than a normal sine wave and more like a natural R-wave. Such wave is generated at 140 BPM, much faster than pre-set pacer rates. It distinguishes between ventricular synchronous and ventricular inhibited pacers and indicates if a ventricular inhibited pacer has a tracking pulse.

Various modifications of the embodiments described and illustrated may be made within the present invention, some of which have already been mentioned. For example, instead of using a single digital display for the various groups of analyzing functions, separate displays may be employed for each group but normally this will not be preferred. Also, instead of having the output connecting terminals to the electrode leads common to both the internal analyzer output for pacing a patient and the electrode analyzing circuitry, separate terminals may be employed, but again this is not usually favored. While it is considered that one electrode/pacer system analyzer should be employed per patient, it is within the invention to utilize a single instrument and adapt it, by means of plural connections, selector switches and protective circuitry, etc., for use with a plurality of patients, electrodes and/or pacers.

In addition to employing the present analyzer for its primary intended purposes, as described, it may also be utilized to measure peak and trailing edge limb lead voltages, as in EKG procedures. The range of BPM from the internal pacer can be broadened, for example, up to 800 BPM, and the pacer may be used for atrial pacing as well as for surpressing arrhythmia. Instead of incorporating a linear type of control for adjusting the internal pacer voltage, used in the determination of threshold voltage, a logarithmic potentiometer can be included in the circuitry (rather than a linear potentiometer) so that initial adjustments in the lower voltage range may be, in effect, fine adjustments, while those at the upper end of the voltage scale will be coarser adjustments. A similar effect can be accomplished mechanically, utilizing a vernier or double dial or control mechanism or the adjustment may be programmed to result in the desired fine-coarse relationship. As a safety feature the switch-through operation of the analyzer, which allows connecting of either the internal or external pacer to the patient, will have incorporated with it switch means for turning off the internal pacer when the external one is connected to the electrode (or the patient).

Although the 4 MV simulated R-wave $sin^2$ pulse go-no go checking for R-wave sensitivity of an external ventricular inhibited pacer is considered acceptable and satisfactory in most applications, it is within the invention to utilize the same type of testing structure with the R-wave amplitude and/or wave shape being adjustable, rather than fixed, so that the minimum amplitude which will inhibit the pacer may be measured and effects of wave structure on the pacer may be followed. Similarly, the pulse width, presently set for either 0.5 or 1 MS, may be varied within the physiological range, either discretely or continuously, so as to adapt the instrument to conform the pulse width to that of any pacing pulse width that might be employed in a pacer to be implanted. Such adjustable pulse width also allows checking the electrode with different pulse widths so as to aid in the selection of the most desirable pacer for implantation.

Because the button selection mechanism of this invention is of an automatic electrical interlock type, rather than of a mechanical type, with the only mechanical function being in the depressing of the selector buttons, the unit lends itself to electronic stepping automation so that test procedures following a form for completion at the time of implantation of a pacer may be automatically followed sequentially. Recording of readings may also be effected automatically, by an automatic printer and/or by electronic storage.

When checking an external pacer, the specifications for which are known, provision can be made for inserting such information into the analyzer and having it compare actually made measurements of pacer characteristics, such as pulse amplitude, width and possibly, even current content, with the specifications or the properties of a standard pacer so that in the event that one of the measured outputs or properties is outside specification, e.g., outside ±10% of specification, the external pacer signal light, which normally flashes in synchronism with the external pacer, remains off.

A variation of the invention with respect to the internal pacer is to include various structures for changing the pacing of the patient, so as to produce, for example, R-wave synchronous, ventricular inhibited, asynchronous, P-wave triggered, P-wave synchronous and AV sequential pacings. The selection of the particular type of pacing could be determined by the doctor so as to improve pacer action, patient comfort and patient safety. Another important safety feature is the inclusion in the apparatus of a timing mechanism so that after a particular length of time, e.g., two minutes, wherein no control (and/or measuring button) has been activated or changed (possibly indicating human error, absence or inattention), when the internal pacer is connected to an implanted electrode the unit will automatically revert to a normal pacemaker output, such as 5 volts at 0.5 MS and 74 BPM, in the ventricular inhibited mode. In such operation it is desirable to have a visual indication, such as a green light, showing that the pacer has reverted to such normal and safe mode. Such mode may also be imposed if, although changes in controls, buttons, etc., have been made within the allowed period, the patient has been unsupported over too long a period of time. In both such instances, it is possible for the surgeon to override the safety mechanism, as by switch activation, but in such override position a warning light is preferably illuminated or another alarm or signal is activated.

The various advantages of the present invention have been described and it should be clear that it is of an improved analyzing instrument of vital importance for use when cardiac pacer implantations are being effected. Extensive tests of the invented analyzer have been undertaken and in uses in conjunction with actual pacer installations in patients it has successfully aided the surgeon. Because of the simple operation of the instrument the taking and recording of various measurements during the implantation operation are facilitated so that excellent records for future reference are easily created and preserved, especially when a standard instruction and report form, normally provided with the instrument, is employed.

The invention has been described with respect to various illustrations and embodiments thereof and also with respect to a drawing of the most preferred embodiment. However, the invention is not to be limited to these because it is evident that one of skill in the art, with the present specification, including the drawing and the claims, before him, will be able to utilize various substitutes and equivalents without departing from the invention.

What is claimed is:

1. An electrode/pacer system analyzer for use when implanting, testing and revising cardiac pacers and electrodes which displays any of a plurality of measurements of pacer and installed electrode functions selectively on a digital display which comprises: pacer analyzing means for measuring and displaying pacer characteristics, including a plurality of measuring circuits for measuring different characteristics of a pacer, a plurality of means for selectively completing the different measuring circuits when a pacer to be tested is connected to the pacer measuring circuit, means for connecting the pacer to be tested to the pacer measuring circuit and digital display means on which the selected pacer analyzer measurements are displayed when selected measuring circuits are completed; electrode analyzing means for measuring and displaying the impedance of an installed cardiac electrode, including a measuring circuit for measuring said impedance, means for completing the measuring circuit when an installed electrode to be tested is connected to the measuring circuit, digital display means for displaying the impedance reading when the measuring circuit is completed and means for connecting the installed cardiac electrode to the electrode measuring circuit; an internal pacer, useful for threshold analysis and for maintaining patient heartbeat, which comprises means for adjusting internal pacer impulse rate, means for adjusting internal pacer voltage, means for measuring at least one of rate, voltage and amperage of the pacer impulses, digital display means for displaying such measurement and means for connecting the implanted electrode to the internal pacer; a rechargeable battery for energizing the pacer analyzing measuring circuit, the electrode analyzing measuring circuit, the internal pacer and the digital display means; means for recharging the rechargeable battery from an external source of electricity; and means for preventing externally supplied battery recharging electric power from communicating with the means for connecting a pacer to be tested to the pacer measuring circuit and the means for connecting an installed cardiac electrode to the electrode measuring circuit.

2. A cardiac electrode/pacer system analyzer according to claim 1 wherein a single digital display is the means for displaying pacer characteristics, installed cardiac electrode impedance and at least one of rate, voltage and amperage of the internal pacer impulses.

3. A cardiac electrode/pacer system analyzer according to claim 2 wherein the impedance measuring circuit includes means for applying a constant current flow while the impedance of the installed electrode is being measured.

4. A cardiac electrode/pacer system analyzer according to claim 3 wherein the electrode analyzing means includes intrinsic and stimulated R-wave measuring means and such measurements are displayed on the digital display.

5. A cardiac electrode/pacer system analyzer according to claim 4 wherein the internal pacer is selectively operable in asynchronous and ventricular inhibited modes.

6. A cardiac electrode/pacer system analyzer according to claim 5 wherein the pacer analyzing means includes means for measuring pacer rate, pulse width peak voltage and trailing edge voltages and such measurements are displayed on the digital display.

7. A cardiac electrode/pacer system analyzer according to claim 6 which includes light emitting diodes for visually indicating external and internal pacer pulses and, in the pacer analyzing means, means for initiating a train of simulated R-waves of the $\sin^2$ type, capable of inhibiting operation of a satisfactorily operating ventricular inhibited pacer and halting the pulsing of the pacer and the pacer pulse light emitting diode to indicate satisfactory sensing of the R-waves by the pacer.

8. A cardiac electrode/pacer system analyzer according to claim 7 comprising switch means for selectively connecting either an external pacer or the internal pacer to an installed cardiac electrode.

9. A cardiac electrode/pacer system analyzer according to claim 8 wherein the plurality of means for selectively completing the plurality of measuring circuits of the pacer analyzing means, the impedance and R-wave measuring circuits of the electrode analyzing means and the rate, voltage and amperage circuits of the internal pacer, are illuminated pushbuttons arranged in separate groupings according to said pacer analyzing, electrode analyzing and internal pacer functions.

10. A cardiac electrode/pacer system analyzer according to claim 9 wherein the electrode analyzing means pushbuttons are color coded differently from the other pushbuttons.

11. A cardiac electrode/pacer system analyzer according to claim 10 which comprises means for varying the pulse width of the pulse generated by the internal pacer.

12. A cardiac electrode/pacer system analyzer according to claim 11 wherein the battery is a nickel-cadmium battery and the means for preventing externally supplied battery recharging electric power from communicating with a pacer to be tested and an installed cardiac electrode, both of which are connected to the cardiac electrode/pacer system analyzer, is an on-off power switch which when it is in on position, connects the nickel-cadmium battery to the circuits of the cardiac electrode/pacer system analyzer except the recharging circuit and when in off position connects only the recharging circuit to said external source of power.

13. A cardiac electrode/pacer system analyzer according to claim 12 wherein separate digital measuring systems, including rate timer, interval timer and sample-hold voltmeter are present in the pacer analyzing means and in the internal pacer so that said systems may be checked against each other by both being employed to measure a characteristic generated by the internal pacer.

14. A cardiac electrode/pacer system analyzer according to claim 13 wherein there are present means for detecting low battery voltage and indicating such low battery voltage condition by flashing of a portion of a digital display and for detecting and indicating lower battery voltage by omitting the display.

15. A cardiac electrode/pacer system analyzer according to claim 14 wherein there are included means for indicating on the digital display erroneous readings, settings and conditions.

16. A cardiac electrode/pacer system analyzer according to claim 15 wherein the R-wave and impedance buttons, when depressed, complete their respective circuits and disconnect the electrode/pacer system internal pacer from the implanted electrode and when released remain illuminated, resuming internal pacer pacing of the implanted cardiac electrode, recording the evoked R-wave on the digital display and maintaining the last measurement corresponding to the impedance on the digital display.

17. A cardiac electrode/pacer system analyzer according to claim 16 comprising a casing which is insulated from all electrical connections to and from the analyzer and from all circuits, controls, indicators and displays thereon and therein.

18. A cardiac electrode/pacer system analyzer according to claim 17 which is sterizable by means of ethylene oxide gas treatment without adversely affecting operation of the analyzer.

19. A cardiac electrode/pacer system analyzer according to claim 1 wherein the impedance measuring circuit includes means for applying constant current flow to the electrode while the impedance of the installed electrode is being measured.

20. A cardiac electrode/pacer system analyzer according to claim 1 wherein the electrode analyzing means includes intrinsic and evoked R-wave measuring means and means for displaying such measurements.

21. A cardiac electrode/pacer system analyzer according to claim 1 wherein the internal pacer is selectively operable in asynchronous and ventricular inhibited modes.

22. A cardiac electrode/pacer system analyzer according to claim 1 which includes light emitting diodes for visually indicating external and internal pacer pulses and, in the pacer analyzing means, means for initiating a train of simulated R-waves capable of inhibiting operation of a satisfactorily operating external ventricular inhibited pacer and halting the pulsing of the pacer and the flashing of the pacer pulse light emitting diode to indicate satisfactory sensing of the R-waves by the pacer.

23. A cardiac electrode/pacer system analyzer according to claim 1 comprising switch means for selectively connecting either an external pacer or the internal pacer to an installed cardiac electrode.

24. A cardiac electrode/pacer system analyzer according to claim 1 wherein the plurality of means for selectively completing the plurality of measuring circuits of the pacer analyzing means, the impedance circuit of the electrode analyzing means and the rate, voltage or amperage circuits of the internal pacer are illuminated pushbuttons arranged in separate groupings according to said pacer analyzing, electrode analyzing and internal pacer functions.

25. A cardiac electrode/pacer system analyzer according to claim 24 wherein the electrode analyzing means includes means for measuring R-waves and the electrode analyzing means pushbuttons are color coded differently from the other push buttons.

26. A cardiac electrode/pacer system analyzer according to claim 1 which comprises means for varying the pulse width of the pulse generated by the internal pacer.

27. A cardiac electrode/pacer system analyzer according to claim 1 wherein the battery is a nickel-cadmium battery and the means for preventing external supplied battery recharging electric power from communicating with the pacer to be tested and an installed cardiac electrode, both of which are connected to the cardiac electrode/pacer system analyzer, is an on-off power switch which, when it is in on position, connects the nickel-cadmium battery to the circuits of the cardiac electrode/pacer system analyzer except the recharging circuit and when in off position connects only the recharging circuit to said external source of power.

28. A cardiac electrode/pacer system analyzer according to claim 1 wherein separate digital measurement systems are present in the pacer analyzing means and in the internal pacer so that said systems may be checked against each other by both being employed to measure a characteristic generated by the internal pacer.

29. A cardiac electrode/pacer system analyzer according to claim 1 wherein the means for completing the circuit for measuring impedance is a depressable button, which, when depressed, completes said circuit and disconnects the electrode/pacer system internal pacer from the implanted electrode and when released, remains illuminated, maintaining the last measurement corresponding thereto on the digital display and resumes internal pacer pacing of the implanted cardiac electrode.

30. A cardiac electrode/pacer system analyzer according to claim 1 wherein the means for selectively completing the different measuring circuits of the pacer analyzing, electrode analyzing and internal pacer sections thereof include an electrical interlock wherein a plurality of measuring circuits is completed rapidly and sequentially, with a circuit being ultimately completed and held in completion being that selected by activation of one of mentioned means.

31. An electrode/pacer system analyzer for use when implanting and testing cardiac pacers and electrodes which displays any of a plurality of measurements of pacer and installed electrode functions selectively on a digital display which comprises: digital display means; means for connection to an external pacer to be implanted; means for connection to a cardiac electrode; pacer analyzing means for measuring and controlling the display of the characteristics of a connected external pacer, including a plurality of measuring circuits for selectively measuring different characteristics of a connected external pacer and means for controlling the display on said digital display of the measurement values; electrode analyzing means for measuring and controlling the display of the impedance of an installed, connected cardiac electrode, including a measuring circuit for measuring said impedance and means for controlling the display on said digital display of the measurement value; an internal pacer, useful for threshold analysis and for maintaining patient heartbeat, which includes means for adjusting internal pacer impulse rate, means for adjusting internal pacer voltage, means for measuring at least one of rate, voltage and amperage of the pacer impulses, and means for controlling the display on said digital display of the measurement value; and switch means for selectively connecting a connected cardiac electrode to said internal pacer and to a connected external pacer.

32. An electrode/pacer system analyzer for use when implanting and testing cardiac pacers and electrodes which displays any of a plurality of measurements selectively on a digital display which comprises: digital display means; means for connection to an external pacer to be implanted; means for connection to a cardiac electrode; pacer analyzing means for measuring and controlling the display of the characteristics of a connected external pacer, including a plurality of measuring circuits for selectively measuring different characteristics of a connected external pacer and means for controlling the display on said digital display of the measurement values; an internal pacer, useful for threshold analysis and for maintaining patient heartbeat, which includes means for adjusting internal pacer impulse characteristics, means for measuring characteristics of the pacer impulses, and means for controlling the display on said digital display of the measurement values; and switch means for selectively connecting a connected cardiac electrode to said internal pacer and to a connected external pacer.

* * * * *